United States Patent
Duerk et al.

(10) Patent No.: US 7,002,342 B2
(45) Date of Patent: Feb. 21, 2006

(54) SYSTEM AND METHOD FOR REDUCING EFFECTS OF ROTATIONAL MOTION

(75) Inventors: Jeffrey L. Duerk, Avon Lake, OH (US); Ajit Shankaranarayanan, East Cleveland, OH (US); Michael Wendt, Iselin, NJ (US); Jonathan S. Lewin, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 76 days.

(21) Appl. No.: 10/475,382

(22) PCT Filed: Apr. 19, 2002

(86) PCT No.: PCT/US02/12278

§ 371 (c)(1),
(2), (4) Date: Oct. 23, 2003

(87) PCT Pub. No.: WO02/085184

PCT Pub. Date: Oct. 31, 2002

(65) Prior Publication Data

US 2004/0145367 A1    Jul. 29, 2004

Related U.S. Application Data

(60) Provisional application No. 60/285,112, filed on Apr. 20, 2001.

(51) Int. Cl.
*G01V 3/00*        (2006.01)

(52) U.S. Cl. .................................................. 324/307
(58) Field of Classification Search ................ 324/307, 324/309; 600/410
See application file for complete search history.

(56) References Cited

U.S. PATENT DOCUMENTS

| | | | | | |
|---|---|---|---|---|---|
| 4,663,591 | A | * | 5/1987 | Pelc et al. | 324/309 |
| 4,720,678 | A | * | 1/1988 | Glover et al. | 324/309 |
| 4,746,860 | A | * | 5/1988 | Satoh | 324/309 |
| 4,751,462 | A | * | 6/1988 | Glover et al. | 324/309 |
| 5,151,656 | A | * | 9/1992 | Maier et al. | 324/309 |
| 5,243,284 | A | * | 9/1993 | Noll | 324/309 |
| 5,545,993 | A | * | 8/1996 | Taguchi et al. | 324/309 |
| 5,810,726 | A | * | 9/1998 | Van Vaals et al. | 600/410 |
| 5,833,609 | A | * | 11/1998 | Dannels et al. | 600/410 |
| 6,404,196 | B1 | | 6/2002 | Duerk et al. | |

OTHER PUBLICATIONS

Thomas Zeffiro, Clinical Functional Image Analysis: Artifact Detection and Reduction, Neuroimage 4, S-95-S100 (1996), Article No. 0059, Academic Press, Inc.

S. Thesen, N. Henselmans, E. Muller, L.R. Schad. Bold Magnetic Resonance Imaging in Real Time. Electromedica 68 (2000) No. 1. Heidelberg, Germany.

C. Weerasinghe, L. Ji and H. Yan. A Novel Motion Estimation Scheme for Rotational Motion Artifact Suppression in MIRI. School of Elec. & Information Eng., Sydney, AU 1999.

(Continued)

*Primary Examiner*—Diego Gutierrez
*Assistant Examiner*—Dixomara Vargas
(74) *Attorney, Agent, or Firm*—John T. Kalnay

(57) ABSTRACT

A method and system for improving image quality by correcting errors introduced by rotational motion of an object being imaged is provided (1150). The method provides a computer executable methodology for detecting a rotation (1110) and selectively reordering (1160), deleting and/or reacquiring projection data (1260).

5 Claims, 18 Drawing Sheets

OTHER PUBLICATIONS

Todd Parrish, Ph.D. Functional Magnetic Resonance Imaging. Dept. of Radiology & Biomedical Engineering, Northwestern Univ.

Wood ML, Shivji MJ, Stanchev PL, Planar-Motion Correction with use of K-Space Data Acquired in Fourier MR Imaging, J Magnetic Reson Imaging 1995; 5:57-64.

Pipe JG. Motion Correction with Propeller MRI: Application to Head Motion and Free-Breathing Cardiac Imaging, Magn Reson Med 1999; 42:963-969.

Korin HW, Felmlee JP, Riederer SJ, Ehman RL. Spatial-Frequency Tuned Markers and Adaptive Correction for Rotional Motion, Magn Reson Med 1995; 33:663-669.

* cited by examiner

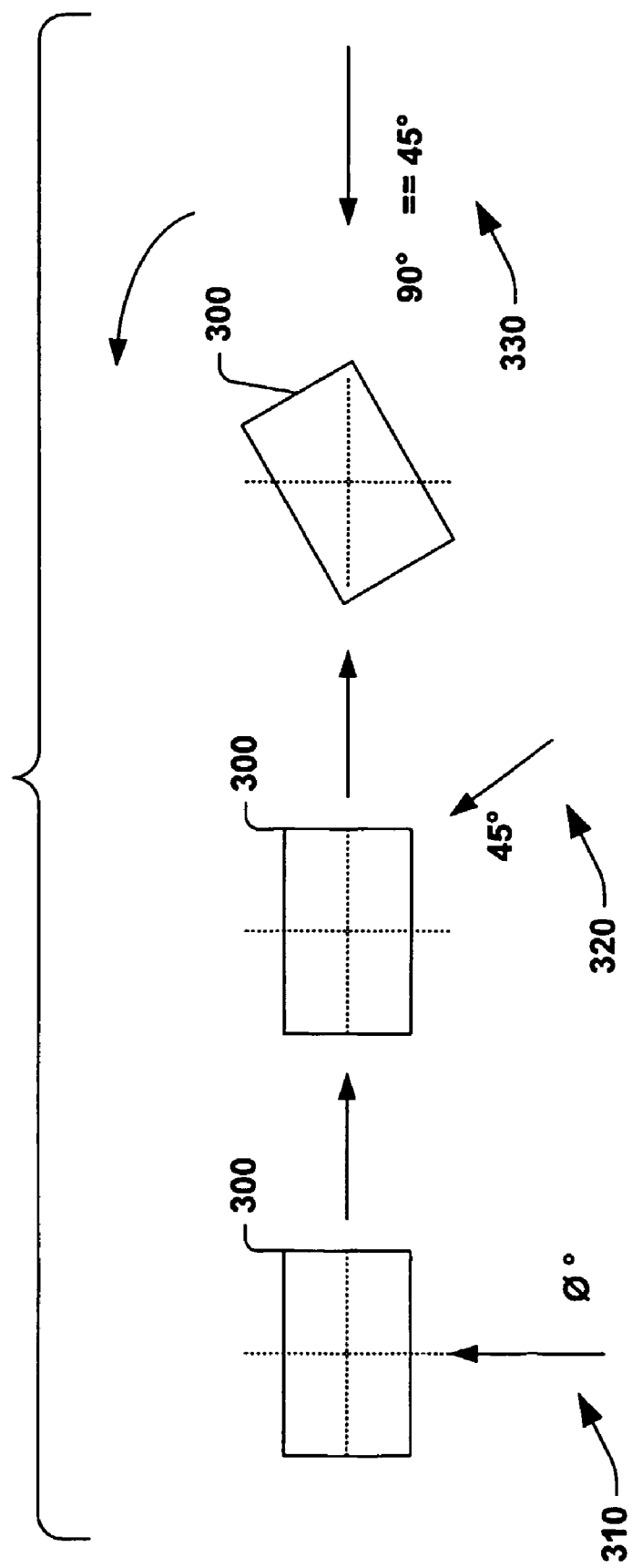

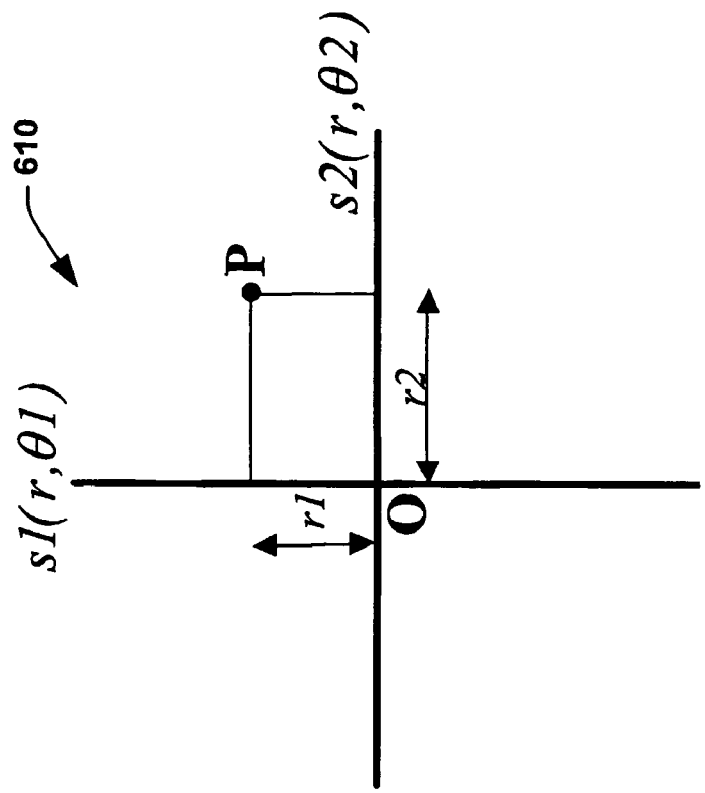
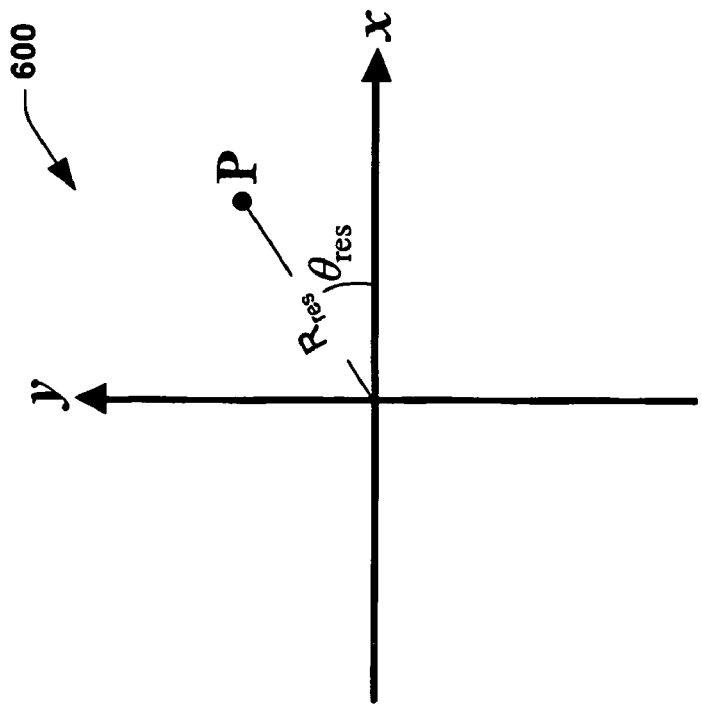
Fig. 6

800

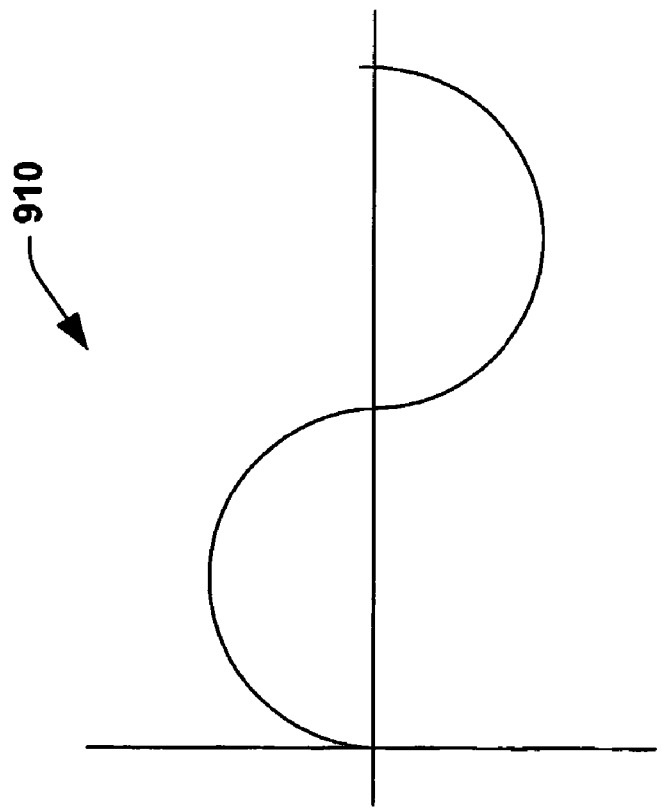
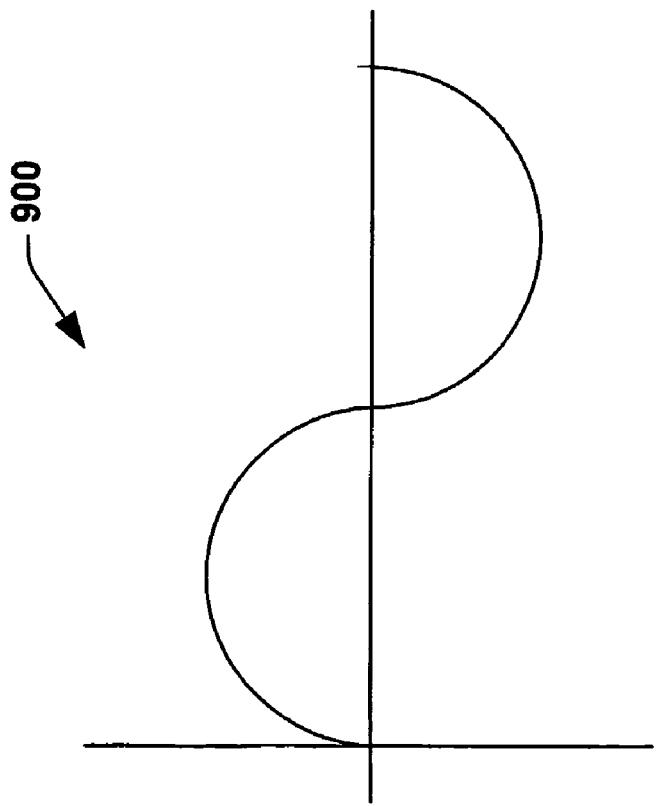
Fig. 9

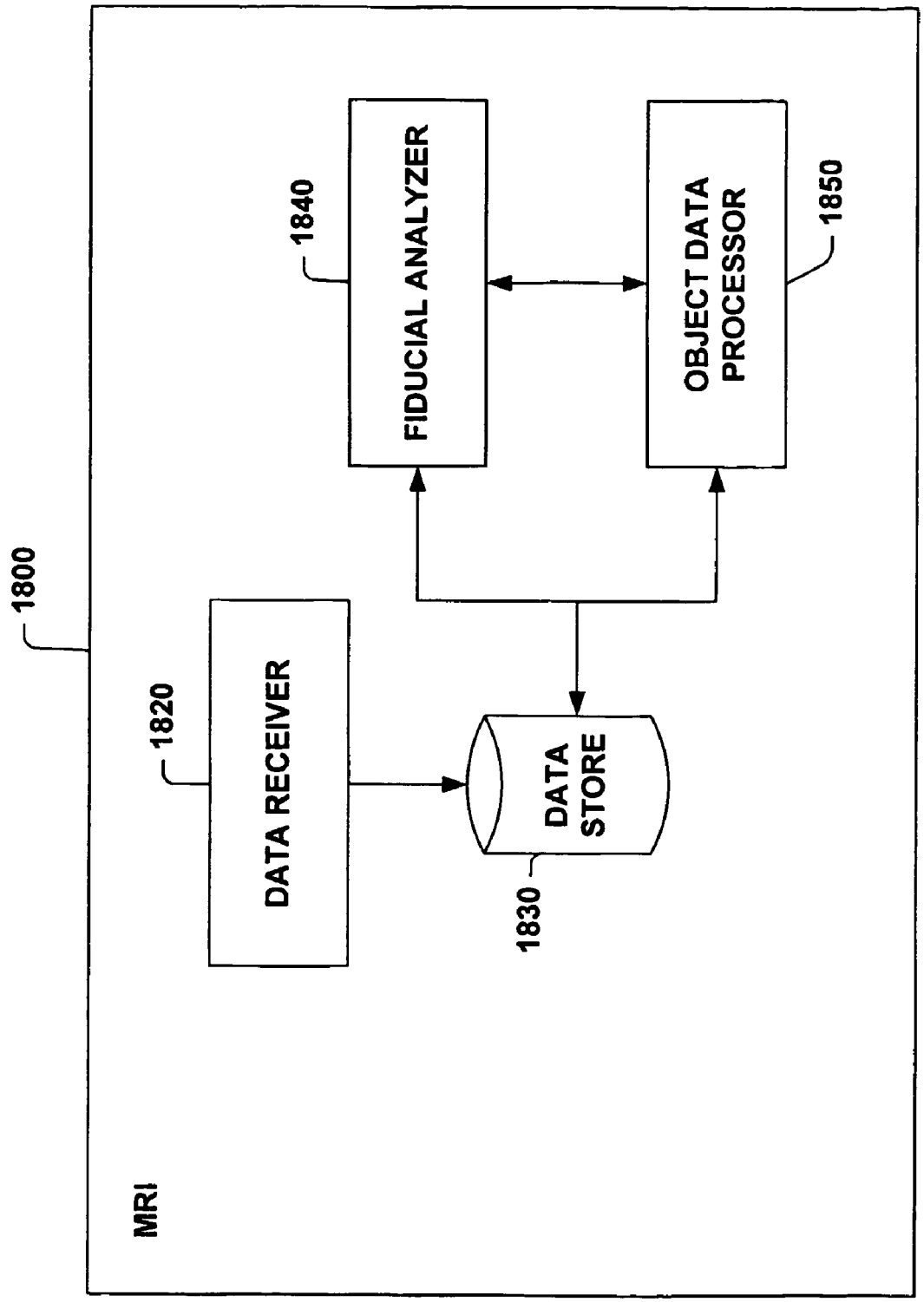

SYSTEM AND METHOD FOR REDUCING EFFECTS OF ROTATIONAL MOTION

CROSS REFERENCE TO RELATED APPLICATIONS

This application claims priority to U.S. Provisional Application 60/285,112 titled "Method and System for Correcting Rotational Motion Artifacts Using Radial K-Space MRI", filed Apr. 20, 2001.

FIELD OF THE INVENTION

The present invention relates to the image processing arts and more particularly to improving magnetic resonance imaging (MRI) system images. It will be appreciated that the invention will also have application to other imaging systems like X-ray, CT, single photon emission computed tomography (SPECT), positron emission tomography (PET), and others.

BACKGROUND

Magnetic resonance imaging systems acquire diagnostic images without relying on ionizing radiation. Instead, MRI employs strong, static magnetic fields, radio-frequency (RF) pulses of energy, and time varying magnetic field gradient waveforms. MRI is a non-invasive procedure that employs nuclear magnetization and radio waves for producing internal pictures of a subject. Two or three-dimensional diagnostic image data is acquired for respective "slices" of a subject area. These data slices typically provide structural detail having, for example, a resolution of one millimeter or better.

Programmed steps for collecting data, which is used to generate the slices of the diagnostic image, are known as a magnetic resonance (MR) image pulse sequence. The MR image pulse sequence includes generating magnetic field gradient waveforms applied along up to three axes, and one or more RF pulses of energy. The set of gradient waveforms and RF pulses are repeated a number of times to collect sufficient data to reconstruct the image slices.

Data is acquired during respective excitations of an MR device. Ideally, there is little or no variation in the nuclear magnetization during the respective excitations. However, movement of the subject caused, for example, by breathing, cardiac pulsation, blood pulsation, and/or voluntary movement, may change the nuclear magnetization from one excitation to the next. This change of the nuclear magnetization may degrade the quality of the MR data used to produce the images Acquiring an MRI image takes a period of time. The period of time is determined, at least in part, by the number of scans that are taken and the number of data acquisitions in each scan. If the object being imaged moves during the scan then artifacts can be introduced into the image. Very small motions (e.g., 1 mm, 1° of rotation) can introduce artifacts like blurring and ghosting. Some patients may have difficulties lying completely still, which can lead to MRI images of these patients being degraded by a rotational motion. Furthermore, some types of motion (e.g., heartbeat, respiration) require additional technologies for reducing the effects on imagery. Since these technologies may not yield ideal results, they too can lead to the degradation of MRI images due to rotational motion.

SUMMARY

The following presents a simplified summary of methods, systems, APIs, data packets, and computer readable media for improving MRI images that are degraded by an object's rotational motion during MRI, to facilitate providing a basic understanding of these items. This summary is not an extensive overview and is not intended to identify key or critical elements of the methods, systems, computer readable media and so on or to delineate the scope of these items. This summary provides a conceptual introduction in a simplified form as a prelude to the more detailed description that is presented later.

This application describes a computer implemented method for reducing the effects on image quality of rotational motion during image acquisition by an MRI system. The method includes receiving data about a fiducial mark associated with the object to be imaged. A point source location of the fiducial can be computed from this point source data and a predicted sine wave in projection data that will be traced by the point source during the acquisition of radial k-space data can be predicted. The method also includes receiving MRI image data of the object. This image data can include, but is not limited to, one or more projections in the radial k-space associated with the object and an observed waveform that can be related to the predicted sine wave. The method also includes comparing the predicted sine wave to the observed waveform and, based on the comparison, selectively processing the image data to reduce the effects of a rotational motion of the object on the image. In one example, the selectively processed image data is then employed to construct a viewable image of the object.

The application also describes a system for improving the quality of an image of an object where the image is degraded by rotational motion of the object during image acquisition. The system includes a data receiver that receives MRI image data from the object being imaged. The image data can include, but is not limited to, object data and fiducial data. The data is stored in one or more data stores, where the object and fiducial data can be stored individually and/or collectively. The system includes a fiducial analyzer that determines a reference sinusoidal fiducial trajectory data and an actual fiducial trajectory data. After these data are computed, the fiducial analyzer compares the actual trajectory data with the reference sinusoidal fiducial trajectory data to determine whether and/or how to selectively manipulate the object data to improve the quality of the image. The determination is based on whether the comparison indicates that the image was degraded by rotational motion of the object during image acquisition.

Certain illustrative example methods, systems, APIs, data packets, and computer readable media are described herein in connection with the following description and the annexed drawings. These examples are indicative, however, of but a few of the various ways in which the principles of the methods, systems, APIs, data packets, and computer readable media may be employed and thus are intended to be inclusive of equivalents. Other advantages and novel features may become apparent from the following detailed description when considered in conjunction with the drawings.

BRIEF DESCRIPTION OF THE DRAWINGS

FIG. 3 illustrates example relationships between viewing angles and rotational corrections.

FIG. 6 illustrates example measurements employed in correcting for rotational motion.

FIG. 9 illustrates two example waveforms, one collected during an MRI and one predicted from a point source data.

FIG. 18 illustrates an example MRI system that includes a data corrector.

DETAILED DESCRIPTION

Figure 1:
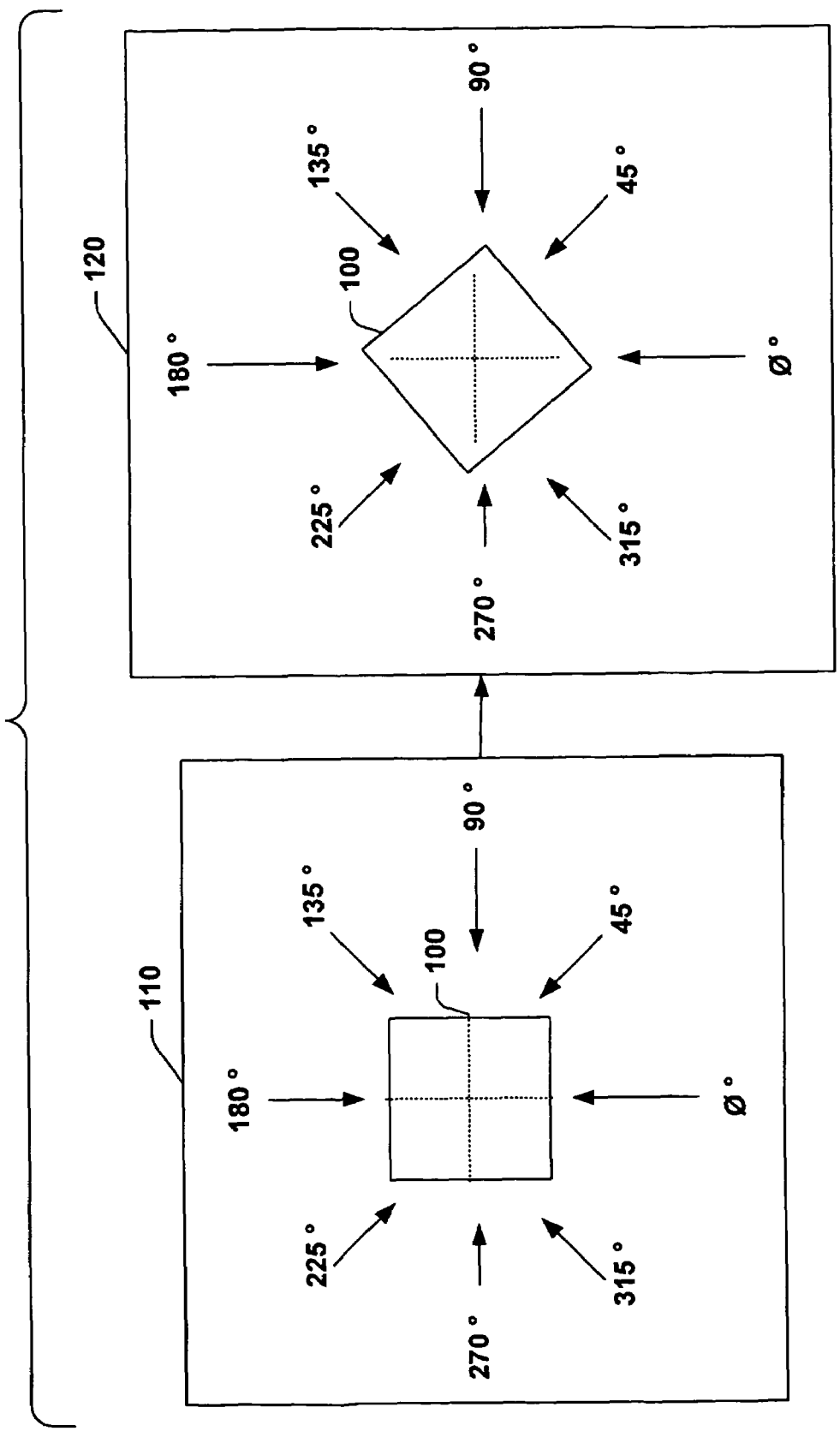
FIG. 1 illustrates example projection angles employed in a radial k-space MRI, and an object before and after rotational motion.

Example methods, systems, APIs, data packets, and computer media are now described with reference to the drawings where like reference numerals are used to refer to like elements throughout. In the following description, for purposes of explanation, numerous specific details are set forth to explain the methods, systems, APIs, data packets, and computer readable media. It may be evident, however, that the methods, systems, APIs, data packets, and computer readable media can be practiced without these specific details. In other instances, well-known structures and devices are shown in block diagram form in order to simplify description.

As used in this application, the term "computer component" refers to a computer-related entity, either hardware, firmware, software, a combination thereof, or software in execution. For example, a computer component can be, but is not limited to being, a process running on a processor, a processor, an object, an executable, a thread of execution, a program and a computer. By way of illustration, both an application running on a server and the server can be computer components. One or more computer components can reside within a process and/or thread of execution and a computer component can be localized on one computer and/or distributed between two or more computers.

"Software", as used herein, includes but is not limited to, one or more computer readable and/or executable instructions that cause a computer or other electronic device to perform functions, actions and/or behave in a desired manner. The instructions may be embodied in various forms like routines, algorithms, modules, methods, threads, and/or programs. Software may also be implemented in a variety of executable and/or loadable forms including, but not limited to, a stand-alone program, a function call (local and/or remote), a servelet, an applet, instructions stored in a memory, part of an operating system or browser, and the like. It is to be appreciated that the computer readable and/or executable instructions can be located in one computer component and/or distributed between two or more communicating, co-operating, and/or parallel processing computer components and thus can be loaded and/or executed in serial, parallel, massively parallel, and other manners.

To facilitate understanding correcting for the rotational motion of an object during radial k-space image acquisition, imagine standing directly in front of a person. You are looking directly at them (e.g., a viewing angle of 0°) and you see their face. For some reason, you want to walk around the person and take 360 photographs, one photograph for each degree of the compass. As you work your way around the person you eventually get exactly half way around (e.g., 180°). Imagine at this point in time, that the person rotates 180° so that you are once again directly face to face. You now move 1° further around your circle and take the next image. While the image is still good data, instead of it being an image taken from 181° (e.g., behind the person you are photographing), it is a repeat of the image from 1°. Thus, when you develop your pictures, you will have two images taken from one degree relative to the face of the person and no images taken 181° relative to the person.

Imagine further that as you reached exactly half way around the person you are photographing, that instead of rotating exactly 180° to face you, they rotate 90° counter to the direction you are walking around them. As you completed your circle around the person, your images would be 90° out of phase. In addition to having 90 duplicate photographs, there would be 90° for which you had no photographs of the person. Thus, the systems and methods described herein facilitate detecting this type of rotational motion, correcting errors in data, and adapting an image acquisition algorithm and/or system to go back and acquire missing view angles. While this analogy describes photography, it is to be appreciated that the present invention relates to MRI, PET, CT, optical imaging and so on, in which projection data are used to reconstruct cross-sectional images.

Referring initially to FIG. 1, two views of an object 100 are illustrated. In the first view 110, the object 100 is at an initial orientation where various projection angles employed in radial k-space MRI are illustrated relative to the object 100. For example, view angles starting at 0° and progressing by 45° to 315° are illustrated. While eight projection angles are illustrated, it is to be appreciated that a greater and/or lesser number of projection angles can be employed in radial k-space MRI. In one example, 360 projection angles can be employed starting at 0° and increasing in one degree increments.

In view 120, the object 100 has undergone rotational motion. Thus, the radial k-space data collected from various projection angles after the rotation may not accurately reflect the projection angle desired. Thus, rotational motion of object 100 during MRI image acquisition can negatively affect image quality.

Figure 2:
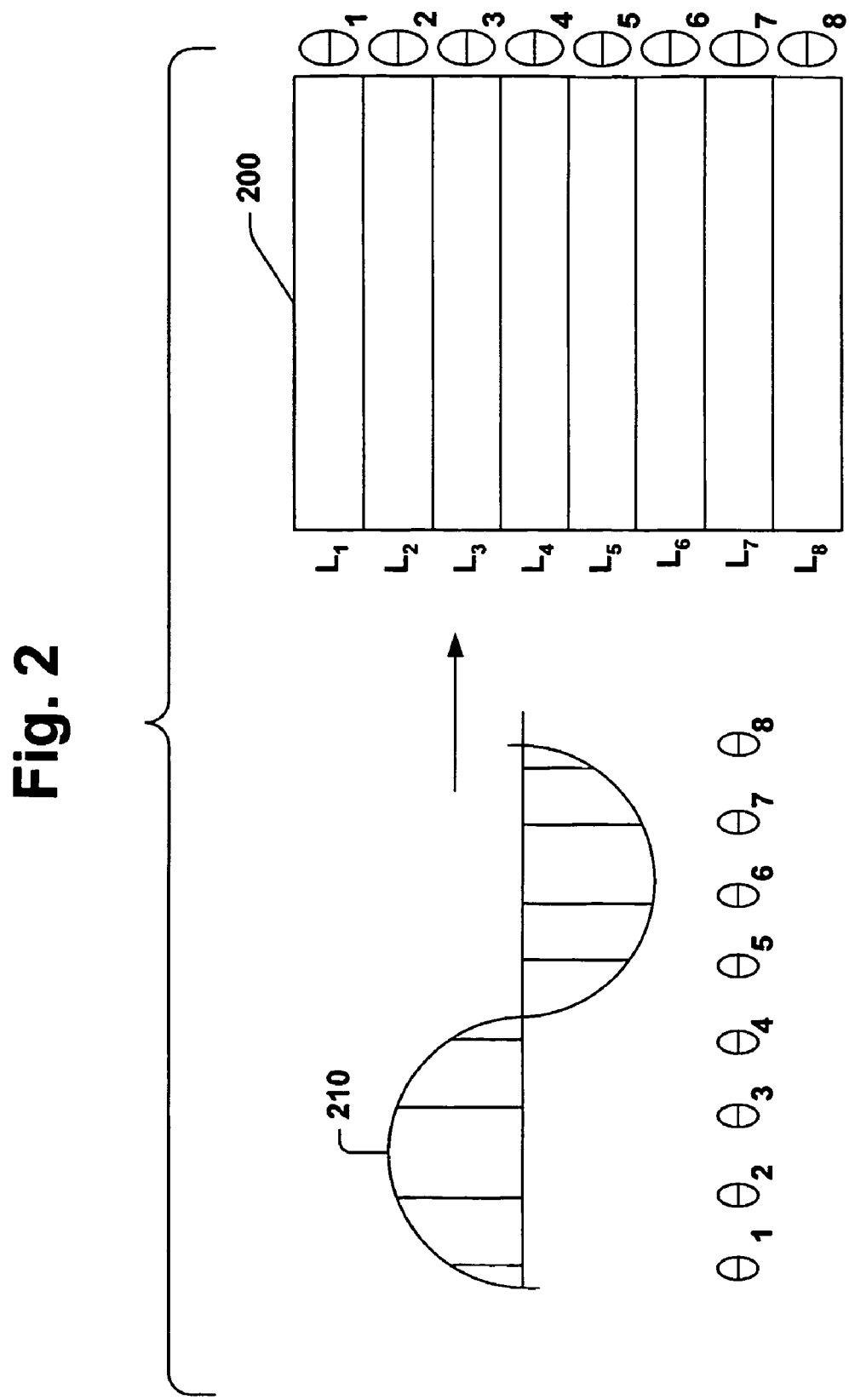
FIG. 2 illustrates an example data structure for storing a set of projection data.

Turning now to FIG. 2, an example data structure 200 that stores a set of projection data 210 is illustrated. The data structure 200 can be, for example, an array addressed to facilitate retrieving projection data by projection angle. For example, a first signal acquired at projection angle $\theta_1$ can be stored in the data structure 200 at location $L_1$. Similarly, a second signal acquired at projection angle $\theta_2$ can be stored in the data structure 200 at location $L_2$. Although the signals can be acquired sequentially (e.g., $\theta_1, \theta_2, \ldots \theta_8$), it is to be appreciated that the data can be acquired in other orders that are neither linear nor sequential. However, storing the data from the various projection angles in the data structure 200 in predetermined locations associated with the programmed projection angles facilitates selectively processing (e.g., re-ordering) the acquired data. While an array is illustrated in FIG. 2, it is to be appreciated that other data structures including, but not limited to, trees, tables, lists, files, and so on, may be employed in accordance with various aspects of this application. The rotational motion described in FIG. 1 can lead to projection data being stored in locations that do not correspond to actual locations, which can negatively affect image quality.

FIG. 3 illustrates example relationships between viewing angles and rotational movements that facilitate correcting for rotational motion during MRI. An object 300 may first be imaged from a viewing angle 0° as illustrated at 310. Data from this view angle can be stored in an addressable data structure at a location programmatically associated with the view angle. Subsequently, the object 300 maybe viewed from an angle of 45° as illustrated at 320. Data from this subsequent view angle can also be stored in an addressable data structure at a location programmatically associated with the subsequent view angle. Thereafter, the object 300 may rotate counterclockwise 45°. If the object 300 were then imaged from an angle of 90° as illustrated at 330, this would be equivalent to re-imaging the object 300 from an angle of 45° as illustrated at 320. Data from this view angle would incorrectly be stored at a location programmatically associated with 90° instead of 45°. Thus, there would be two sets of data for the projection angle of 45° (one stored correctly, one stored incorrectly) and no projection data for the projection angle of 90°. In conventional systems that do not account for the rotational motion of the object 300, the data assumedly acquired at 90° would be incorrectly stored for the 90° projection angle. The systems and methods described herein facilitate detecting rotational motion of the object 300 and determining where, if anywhere, the unanticipated projection angle data should be stored and how it should be processed.

Figure 4B:
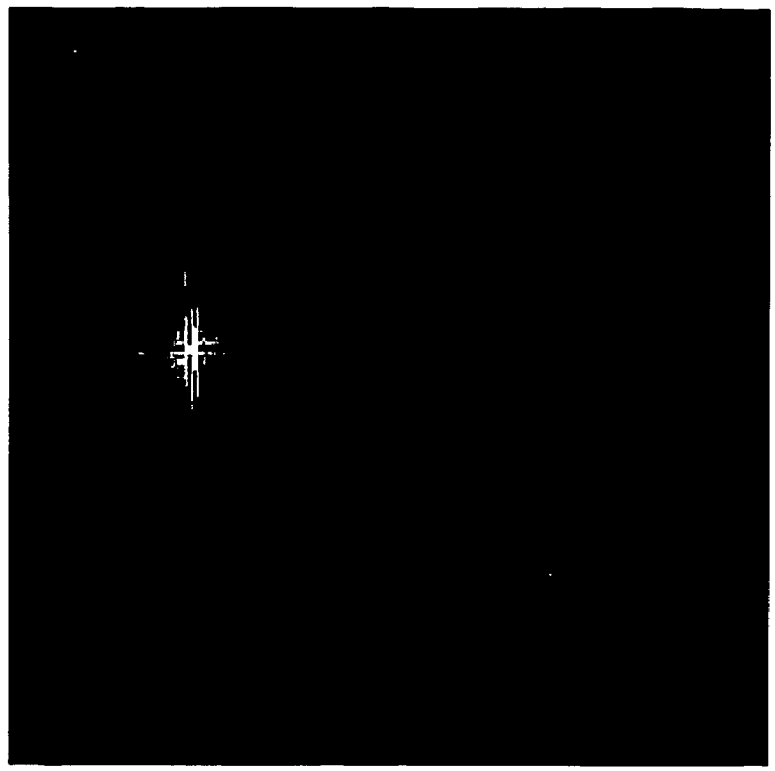
FIGS. 4a and 4b illustrate example MRI images before and after correction for rotational motion.
Figure 4A:
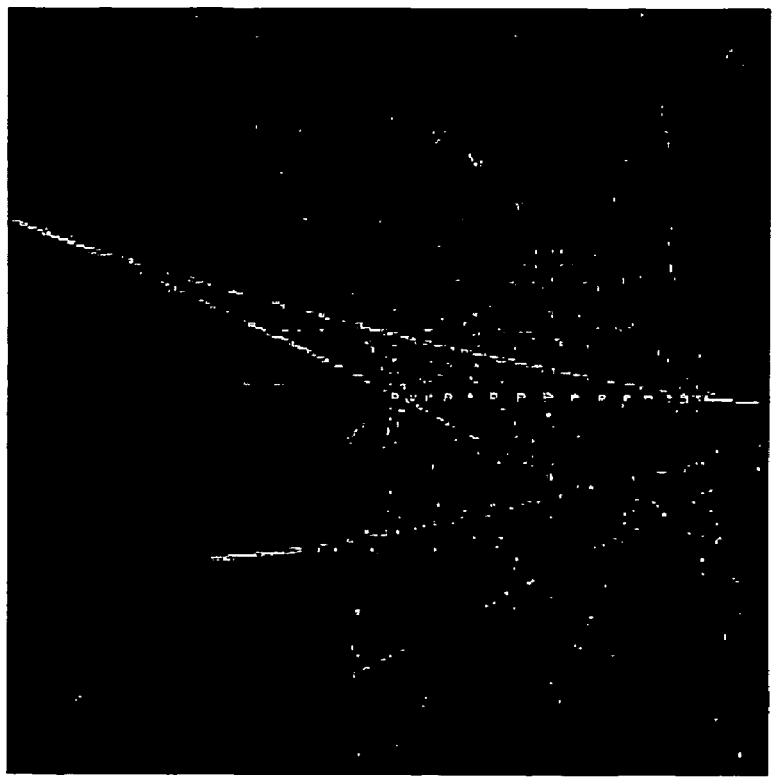

Turning now to FIGS. 4a and 4b, two images illustrate example MRI images before (FIG. 4a) and after (FIG. 4b) correction for rotational motion. Image 400 is an MRI image before correction, where the image is degraded due to rotational motion of the object during image acquisition. Image 410 is an MRI image of the same item after detecting errors due to rotational motion and correcting for those errors. A bright spot in the top center of image 410 represents an image marker placed on or near but linked to the object. This will be described in greater detail below.

Figure 5B:
FIGS. 5a and 5b illustrates example MRI images before and after correction for rotational motion
Figure 5A:
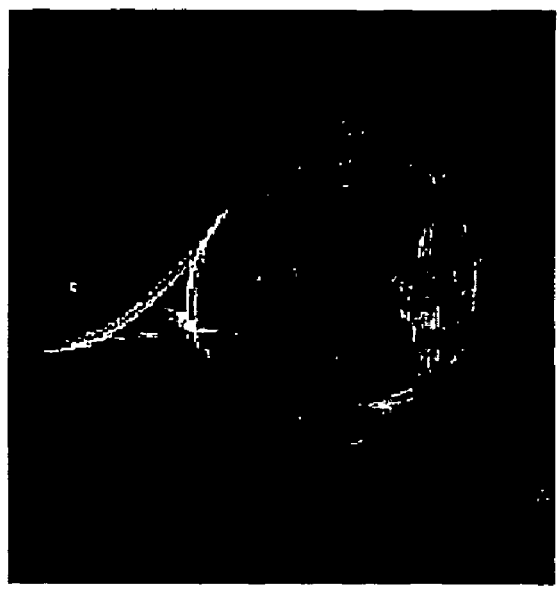

FIGS. 5a and 5b similarly illustrate before and after representations of MRI images. For example, image 500 is an uncorrected image of a knee that rotated during the acquisition of the MRI image. Image 510 is an image of the knee after the rotational motion has been detected and corrective steps have been taken. Again, notice the bright spot in the top center of image 510. The bright spots in FIGS. 4b and 5b are associated with a fiducial mark associated with the object to be imaged. In one example, a high signal fiducial mark can be employed, where the high signal fiducial mark is a gadolinium filled tuned fiducial marker that facilitates receiving fiducial data from an object being imaged. It is to be appreciated that while the fiducial mark may be placed on the object to be imaged, the fiducial may also be placed near the object to be imaged and/or can be associated with the object to be imaged so that it if the object rotates the fiducial will also rotate. It is to be further appreciated that more than one fiducial may be associated with the object to be imaged, which would produce one or more reference waveforms that could be analyzed by the systems and methods described herein.

Figure 7:
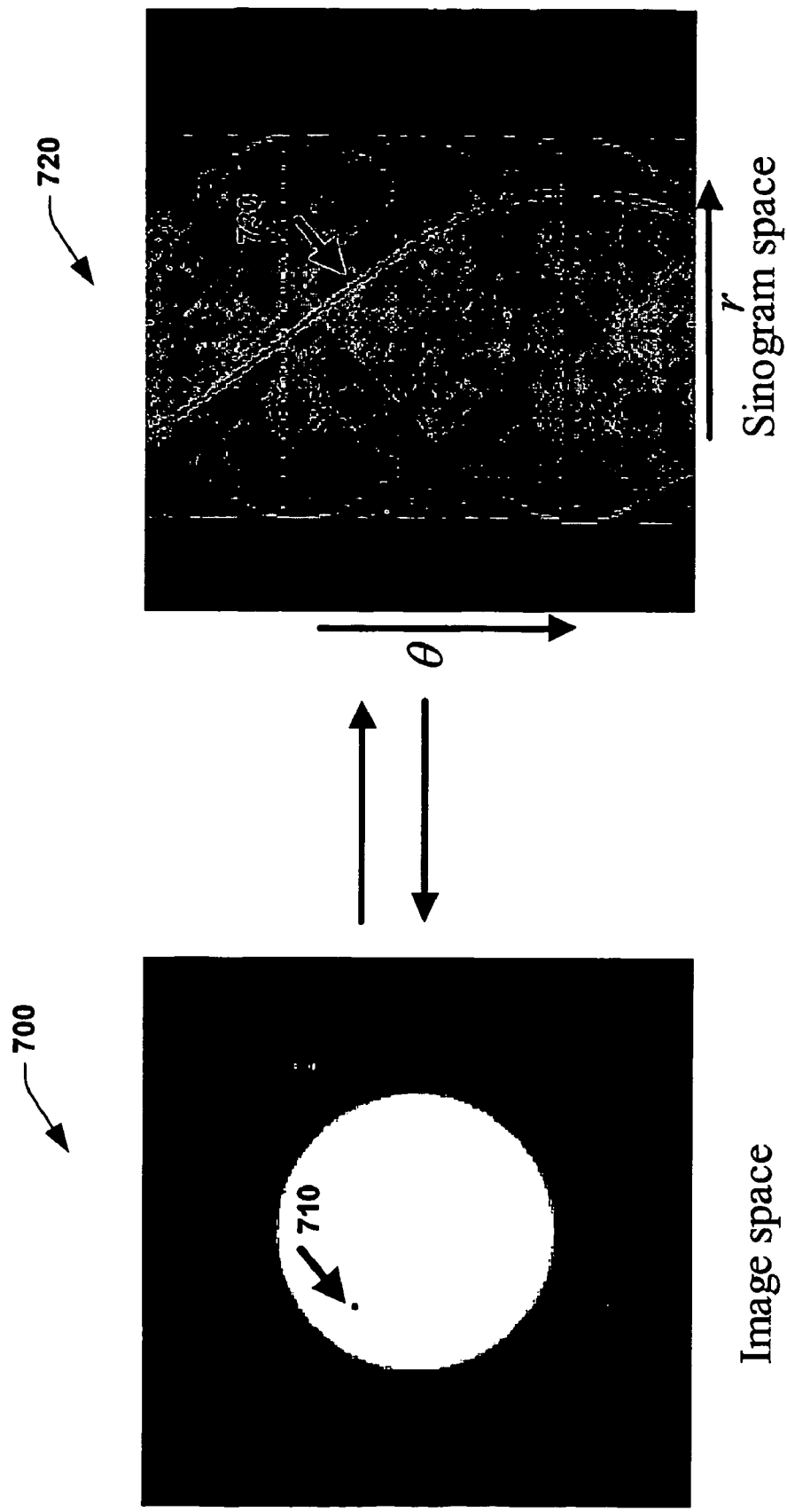
FIGS. 7a and 7b illustrate an example point source, image space, and sinogram space.

FIGS. 6, 7a, and 7b show a relationship between an image space and a sinogram space. A sinogram is a two-dimensional map representing the amplitude of a signal as a function of its position along a projection direction along one axis, with the other axis representing the projection angle. Note that a point source in the image space transforms into a unique sine wave in the sinogram space. This sine wave can also be recreated from, at minimum, two projections. This is a direct result of Shannon's sampling theorem. For example, take two projections of a point source P, s1(r, $\theta_1$) and s2(r, $\theta_2$), at angles $\theta_1=0°$ and $\theta_2=90°$, respectively. Illustration 600 shows the imaging coordinate system and the point source P. Illustration 610 shows the two projections about the center of rotation O. r1 and r2 represent the projected distance of P on s1 and s2, respectively, from the center of rotation of the projections, O. If this point source rotates with the imaged object during the acquisition of the radial data, the sine wave corresponding to the point source will be disrupted. The disrupted waveform can, theoretically, be extracted from the sinogram data, using an edge detection algorithm and/or other detection algorithm, methods, apparatus and processes.

FIG. 6 illustrates fiducial mark measurements that facilitate detecting and/or correcting for rotational motion of an object being imaged. Illustrations 600 and 610 show a point P that is associated with the fiducial mark. A first projection taken at a viewing angle of $\theta_1$ results in a projection data $S_1$ from which a projection distance $r_1$ can be computed. A second projection taken at a viewing angle of $\theta_2$ yields a second projection data $S_2$ from which a second projected distance $r_2$ can be acquired. This first projection data and second projection data can be referred to as a point source data. In one example, the viewing angles $\theta_1$ and $\theta_2$ are orthogonal to each other, which facilitates subsequent rotational motion detection and correction. While two projection data are illustrated at 610, it is to be appreciated that a greater number of projections can be employed to produce the point source data. Additionally, it is to be appreciated that the projection data that forms the point source data can be acquired at times including, but not limited to, before imaging the object, while acquiring the MRI image, and after acquiring the MRI image. In one example, the first projection data $S_1$ and the second projection data $S_2$ are repetitively acquired until it is mathematically verifiable that no rotational motion occurred between acquiring the two data. This facilitates detecting and correcting for rotational motion of an imaged object.

Once the point source data has been acquired, then a point source location can be computed from the point source data. For example, in illustration 600, a $\theta_{res}$ and an $R_{res}$ can be computed from $S_1$ and $S_2$ to simplify subsequent mathematical calculations employed in detecting and correcting for rotational motion. In one example, $R_{res}$ is determined according to $R_{res}$=the square root of $(r_1^2+r_2^2)$. Similarly, in one example, $\theta_{res}$ is determined according to $\theta_{res}=\tan^{-1}(r_2/r_1)$. Once $\theta_{res}$ and $R_{res}$ have been computed, a predicted sine wave that will be traced by the fiducial mark can be computed. In one example, the predicted sine wave is calculated according to $\sin_{res}=(R_{res})\cos(|\theta_{res}-\theta|)$, where $\theta$ can vary throughout a range of viewing angles.

Thus, referring to the calculations associated with FIG. 6, two projections are taken at viewing angles $\theta_1$ and $\theta_2$, preferably where $\theta_1$ and $\theta_2$ are orthogonal. Preferably, the projections are taken at times between which it can be determined that no rotational motion occurred. Given the two projection data, the values $R_{res}$ and $\theta_{res}$ can be computed. Once $R_{res}$ and $\theta_{res}$ are computed, then a predicted reference waveform that will be produced from the signal generated by the fiducial marker can be computed.

Turning now to FIGS. 7a and 7b, an example point source and the sinogram resulting from a radial k-space data acquisition of an image associated with the point source is presented. In addition to the point source data, data associated with the object with which the point source is associated is also stored. If the system computes how far from an expected location the point source has rotated, then a computation can be made to determine how far to shift the data associated with both the point source and the object to correct for the rotational motion. Thus, a method employing an object associated with a fiducial can include associating the point source 710 with the object to be imaged, computing the point source location, predicting a sine wave 730 that will be produced during radial k-space acquisition of the object data, acquiring a unique actual waveform from the radial projections, comparing the predicted sine wave 730 to the actual unique waveform that is collected during MRI and correcting and/or reacquiring data based on the comparison of the predicted sine wave 730 to the actual waveform.

Figure 8:
FIG. 8 illustrates an example sinogram exhibiting the results of rotational motion on a reference waveform.

FIG. 8 illustrates an example sinogram exhibiting a result of rotational motion on a reference waveform 800. The reference waveform 800 (brightest line) illustrates a step discontinuity characteristic of a rotational motion of the fiducial marker associated with the object to be imaged. An edge detection algorithm (or other detection method/apparatus) can be used to detect the step discontinuity. By detecting the discontinuity in the reference waveform 800, both the point at which rotational motion occurred, the point at which the object rotated back (if any), and the amount of rotational motion can be computed. While a step discontinuity is illustrated in FIG. 8, it is to be appreciated that other deformations and/or irregularities in an acquired waveform may also be detected.

FIG. 9 illustrates two waveforms. The sine wave 900 is an example of a predicted sine wave while the waveform 910 is an example of an actual waveform acquired during radial k-space MRI. The systems and methods described herein predict the sine wave 900, acquire the waveform 910, and compare the two waveforms to determine whether the data points are within a predetermined, configurable tolerance. If the waveforms are within the tolerances, then the systems and/or methods can proceed to subsequent steps like reconstructing an image from the acquired MRI data. If, however, the comparison produces data outside the tolerances, then additional processing like selective processing of the image data can be undertaken to correct for rotational motion during image acquisition, which is described in greater detail below.

Figure 10:
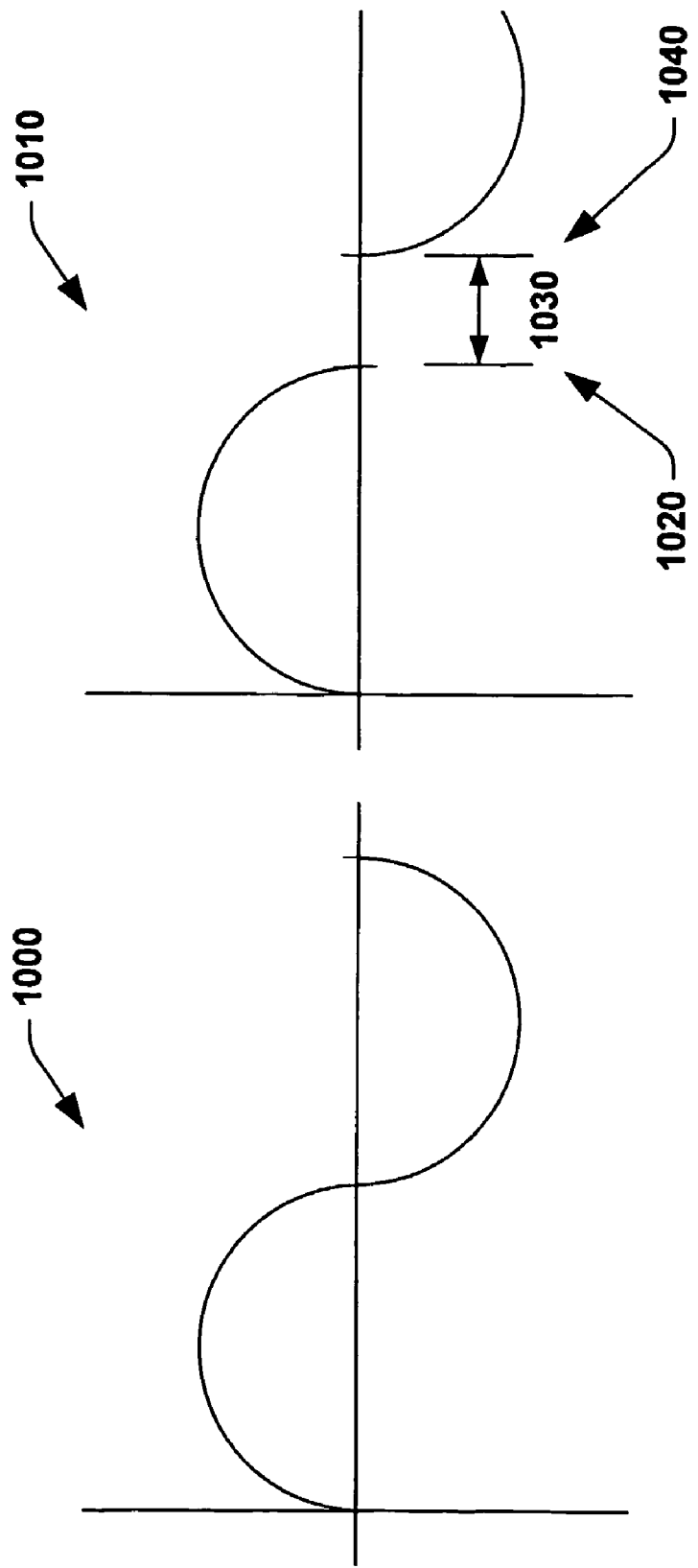
FIG. 10 illustrates two example waveforms, one predicted from a point source data and one collected during an MRI, where the collected waveform exhibits the results of rotational motion during image acquisition.

Turning to FIG. 10, an example waveform 1010 collected during an MRI where the wave exhibits the results of rotational motion is illustrated alongside a predicted sine wave 1000. The predicted sine wave 1000 was computed from point source data acquired from a fiducial associated with the object to be imaged. The actual wave 1010 was then collected from the MRI data. As seen, the actual wave 1010 is distorted starting at an identifiable point 1020 at which a rotational motion occurred. Furthermore, the disrupted wave 1010 facilitates identifying a point 1040 at which the rotational motion ceased. The interval 1030 facilitates identifying, for example, the magnitude and/or direction of the rotation. As described earlier, a rotational motion can lead to gaps in the projection data and/or duplicate projection data. Therefore, based on the location 1020, the interval 1030, and the location 1040, data from the MRI of the object can be selectively processed to correct the rotational motion. The selective processing can include, but is not limited to, re-ordering the data, removing one or more projection data from the set of projection data acquired during MRI, and generating a signal to indicate that additional projection data should be acquired. When a signal is generated to indicate that additional projection data should be acquired, systems and methods described herein may then receive the additional projection data and update the data that produced wave 1010 to facilitate recomparing the predicted sine wave with an updated waveform. In one example, the steps of generating a signal to indicate that additional projection data should be acquired, receiving the additional projection data, updating the observed waveform, and reperforming the comparison of the predicted sine wave with the updated waveform can occur repeatedly. For example, they may repeat until a comparison of the predicted sine wave and the updated observed waveform is within a predetermined configurable tolerance and/or until a predetermined, configurable number of attempts have been made.

Since the comparison of the predicted sine wave with the acquired waveform can be performed by distributed systems and/or methods operating substantially in parallel with an MRI system, which may be distinct from the systems for acquiring the MRI data, it is to be appreciated that the systems and methods described herein for detecting rotational motion of an object should not increase MRI scan times. While the computations do not increase the scan time, one example method facilitates improving a signal to noise ratio in the observed image data by at least 50%. By recognizing the location, direction, and magnitude of a rotational motion, "errors" can be removed from acquired data which leads to the improvement in the signal to noise ratio. In another example, systems and methods described herein facilitate improving the signal to noise ratio in the selectively processed observed image data to within 33% of what the signal to noise ratio would be in a corresponding image data that was not disrupted by rotational motion. The ability to undertake processing like removing duplicate data, averaging duplicate data, acquiring data that was initially missed, re-ordering data that has been stored in an incorrect location, and the like, facilitates producing these improvements in general image quality. Such improvements can be measured by measurements including, but not limited to, signal to noise ratios, resolution, level of artifacts, and so on.

As described above, the observed image data received from an MRI scan of an object includes the projection data of a radial k-space associated with the object and an observed waveform associated with the fiducial associated with the object that is scanned. However, the data associated with the fiducial may leave an artifact in the observed image data. Therefore, in one example method, additional processing is performed to remove the waveform data from the image data associated with the fiducial.

While the systems and methods described herein facilitate identifying and correcting for rotational motion during image acquisition, it is to be appreciated that once such detection and correction have been undertaken, example systems and methods may subsequently construct an image of the object based on observed image data that has been selectively processed to correct for rotational motion. It is to be further appreciated that the processing performed to correct for rotational motion during image acquisition may be employed in systems and methods that also undertake processing designed to reduce the effects of translational motion of the object to be imaged. In one example, the translational motion correction is undertaken before the correction for rotational motion.

Figure 11:
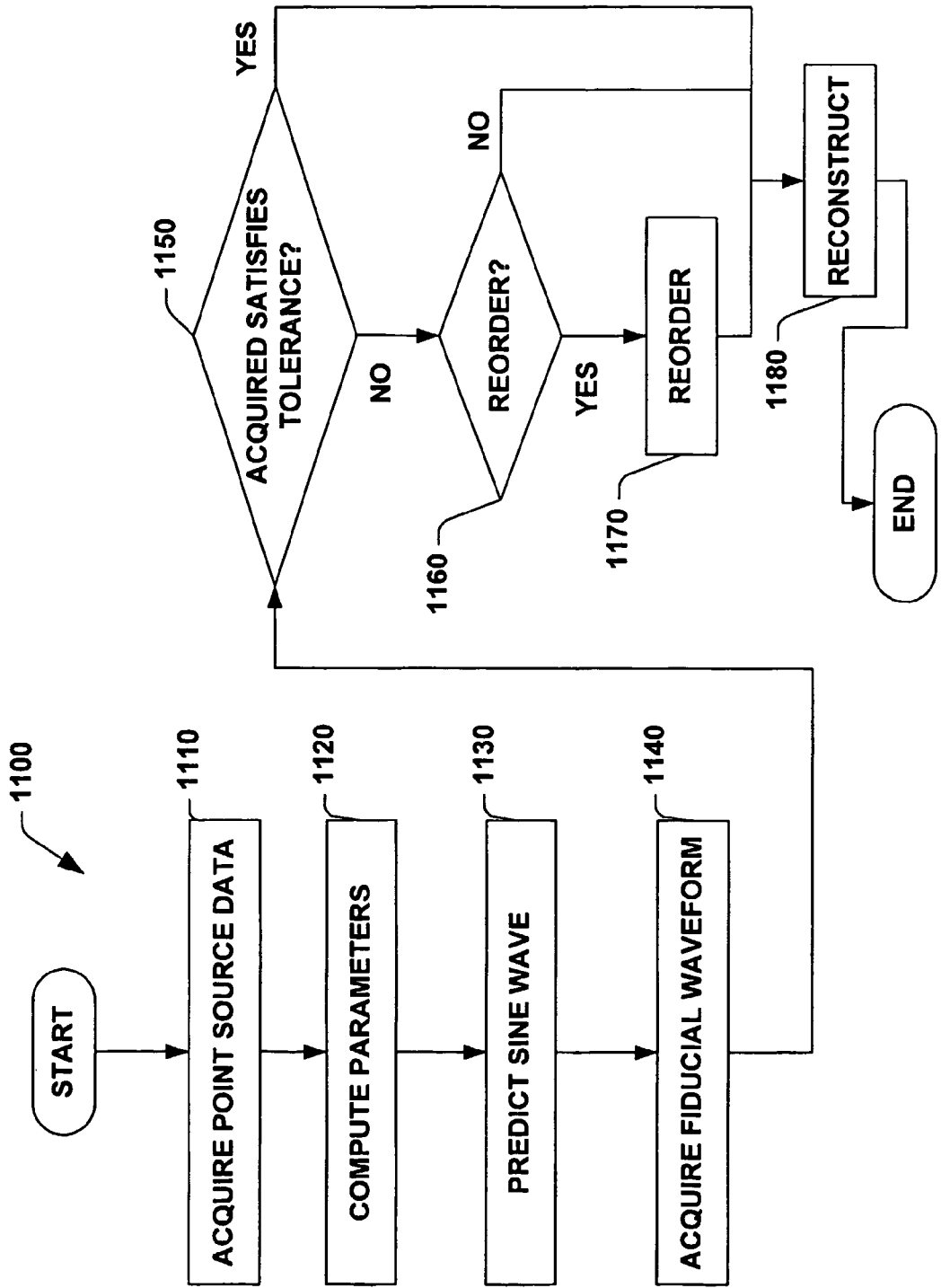
FIG. 11 illustrates an example method for reducing the effects on image quality of rotational motion of an object during image acquisition.
Figure 12:
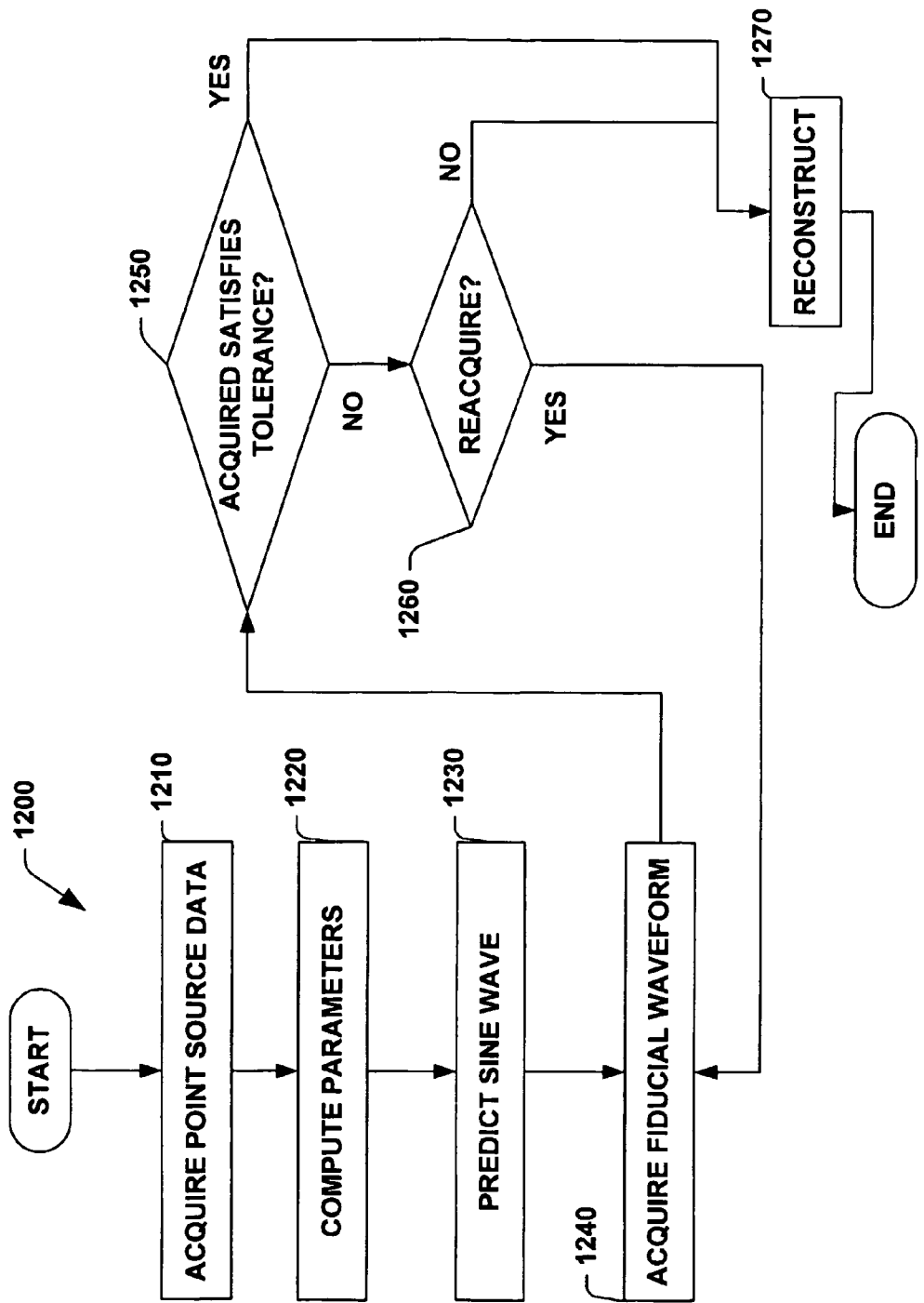
FIG. 12 illustrates an example method for reducing the effects on image quality of rotational motion of an object during image acquisition.

In view of the exemplary systems shown and described herein, example computer implemented methodologies will be better appreciated with reference to the flow diagrams of FIGS. 11 and 12. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Furthermore, additional and/or alternative methodologies can employ additional, not illustrated blocks. In one example, methodologies are implemented as computer executable instructions and/or operations stored on computer readable media including, but not limited to an application specific integrated circuit (ASIC), a compact disc (CD), a digital versatile disk (DVD), a random access memory (RAM), a read only memory (ROM), a programmable read only memory (PROM), an electronically erasable programmable read only memory (EEPROM), a disk, a carrier wave, and a memory stick. It is to be appreciated that the methodologies can be implemented in software as that term is defined herein.

In the flow diagrams, rectangular blocks denote "processing blocks" that may be implemented, for example, in software. Similarly, the diamond shaped blocks denote "decision blocks" or "flow control blocks" that may also be implemented, for example, in software. Alternatively, and/or additionally, the processing and decision blocks can be implemented in functionally equivalent circuits like a digital signal processor (DSP), an application specific integrated circuit (ASIC), and the like.

A flow diagram does not depict syntax for any particular programming language, methodology, or style (e.g., procedural, object-oriented). Rather, a flow diagram illustrates functional information one skilled in the art may employ to program software, design circuits, and so on. It is to be appreciated that in some examples, program elements like temporary variables, routine loops, and so on are not shown.

Referring now to FIG. 11, a flow chart illustrates an example method 1100 for reducing the effects on image quality of rotational motion of an object during MRI image acquisition. At 1110, point source data is acquired. This point source data can include measurements like the angles of projection employed in characterizing the point source, and resulting distances associated with characterizing the point source.

At 1120, point source parameters can be computed. For example, parameters $R_{res}$ and $\theta_{res}$ can be computed from the point source data acquired at 1110. At 1130, based, at least in part, on the parameters computed at 1120 and/or the point source data acquired at 1110, a unique sine wave that will be produced by the point source during radial k-space MRI can be predicted. At 1140, waveform data associated with the point source is acquired from the object being imaged. While blocks 1130 and 1140 illustrate predicting the sine wave and then acquiring the waveform data, it is to be appreciated that such predictions and acquisitions can occur substantially in parallel.

At 1150, a determination is made concerning whether the acquired waveform data satisfies pre-determined, configurable tolerances when compared to the predicted sine wave data. For example, the sum of the absolute values of the differences of predicted points on a sine wave with acquired points on a waveform can be computed. If the determination at 1150 is yes, then processing proceeds to 1180 where the object image is reconstructed from the acquired data. However, if the determination at 1150 is no, then at 1160 a determination is made concerning whether to re-order one or more projection data points. If the determination at 1160 is yes, then the projection data will be re-ordered. For example, data placed in a first location corresponding to a first, incorrect view angle may be moved to a second, correct view angle location. Additionally, and/or alternatively, the data may be averaged with data already stored in the correct view angle location, may replace the data already stored in the correct view angle location or may be employed to correct data stored in the correct view angle location. The determination at 1160 may be no if, for example, the differences between the predicted sine wave data and the acquired waveform data exceed a predetermined, configurable threshold indicating that re-ordering would not produce a desired reduction in signal to noise ratio. In such a case, method 1100 may be extended to include restarting the image acquisition sequence.

FIG. 12 illustrates an example method 1200 for reducing the effects on image quality of rotational motion of an object during MRI image acquisitions. While the methods 1100 and 1200 are discussed in connection with MRI, it is to be appreciated that the systems and methods described herein can be employed where an object is imaged through techniques including, but not limited to, magnetic resonance imaging, x-ray imaging, CT, SPECT, optical imaging techniques and positron emission tomography. The optical imaging techniques can include, but are not limited to techniques involving bio-luminescence and fluorescence.

At 1210, point source data is acquired and at 1220 point source parameters are computed from the point source data. Thus, the location of a fiducial associated with an object to be imaged can be computed which facilitates, at 1230, predicting a unique sine wave that will be produced during the imaging of the object. At 1240, observed waveform data from the fiducial mark is acquired. Thus, at 1250, a determination is made concerning whether the acquired waveform data is within predetermined, configurable tolerances of the sine wave predicted at 1230. If the determination at 1250 is yes, then processing continues at 1270 where the image of the object is reconstructed. If, however, the determination at 1250 is no, then at 1260, a determination is made concerning whether to reacquire one or more points of waveform data by, for example, repositioning imaging means that selectively acquire one or more projection data from one or more viewing angles. If the determination at 1260 is no, then at 1270, an image of the object is reconstructed. But if the determination at 1260 is yes, then processing returns to 1240. In one example method, the determination at 1260 may depend, at least in part, on a predetermined, configurable number of attempts having been made to reacquire data and/or whether the method 1200 should be restarted.

Figure 13:
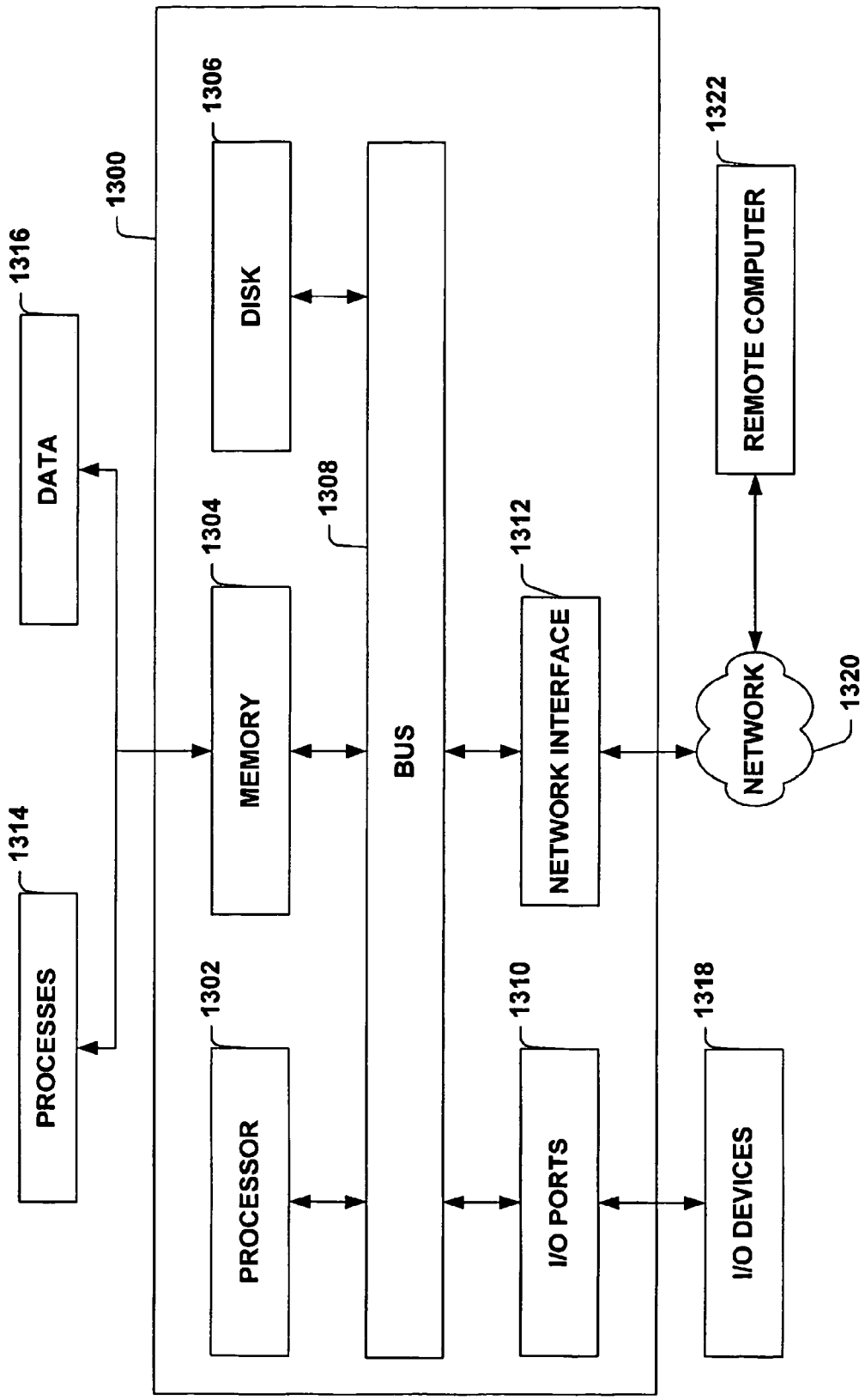
FIG. 13 is a schematic block diagram of an example computing environment with which the systems, methods, APIs, data packets, and computer readable media described herein may interact.

FIG. 13 illustrates a computer 1300 that includes a processor 1302, a memory 1304, a disk 1306, input/output ports 1310, and a network interface 1312 operably connected by a bus 1308. Executable components of the systems described herein may be located on a computer like computer 1300. Similarly, computer executable methods described herein may be performed on a computer like computer 1300. It is to be appreciated that other computers may also be employed with the systems and methods described herein. Furthermore, it is to be appreciated that the computer 1300 can be located locally to an MRI system, remotely to an MRI system and/or can be embedded in an MRI system.

The processor 1302 can be a variety of various processors including dual microprocessor and other multi-processor architectures. The memory 1304 can include volatile memory and/or non-volatile memory. The non-volatile memory can include, but is not limited to, read only memory (ROM), programmable read only memory (PROM), electrically programmable read only memory (EPROM), electrically erasable programmable read only memory (EEPROM), and the like. Volatile memory can include, for example, random access memory (RAM), synchronous RAM (SRAM), dynamic RAM (DRAM), synchronous DRAM (SDRAM), double data rate SDRAM (DDR SDRAM), and direct RAM bus RAM (DRRAM). The disk 1306 can include, but is not limited to, devices like a magnetic disk drive, a floppy disk drive, a tape drive, a Zip drive, a flash memory card, and/or a memory stick. Furthermore, the disk 1306 can include optical drives like, a compact disk ROM (CD-ROM), a CD recordable drive (CD-R drive), a CD rewriteable drive (CD-RW drive) and/or a digital versatile ROM drive (DVD ROM). The memory 1304 can store processes 1314 and/or data 1316, for example. The disk 1306 and/or memory 1304 can store an operating system that controls and allocates resources of the computer 1300.

The bus 1308 can be a single internal bus interconnect architecture and/or other bus architectures. The bus 1308 can be of a variety of types including, but not limited to, a memory bus or memory controller, a peripheral bus or external bus, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial bus (USB), and a small computer systems interface (SCSI) bus.

The computer 1300 interacts with input/output devices 1318 via input/output ports 1310. Input/output devices 1318 can include, but are not limited to, a keyboard, a microphone, a pointing and selection device, cameras, video cards, displays, and the like. The input/output ports 1310 can include but are not limited to, serial ports, parallel ports, and USB ports.

The computer 1300 can operate in a network environment and thus is connected to a network 1320 by a network interface 1312. Through the network 1320, the computer 1300 may be logically connected to a remote computer 1322. The network 1320 includes, but is not limited to, local area networks (LAN), wide area networks (WAN), and other networks. The network interface 1312 can connect to local area network technologies including, but not limited to, fiber distributed data interface (FDDI), copper distributed data interface (CDDI), ethernet/IEEE 802.3, token ring/IEEE 802.5, and the like. Similarly, the network interface 1312 can connect to wide area network technologies including, but not limited to, point to point links, and circuit switching networks like integrated services digital networks (ISDN), packet switching networks, and digital subscriber lines (DSL).

Figure 14:
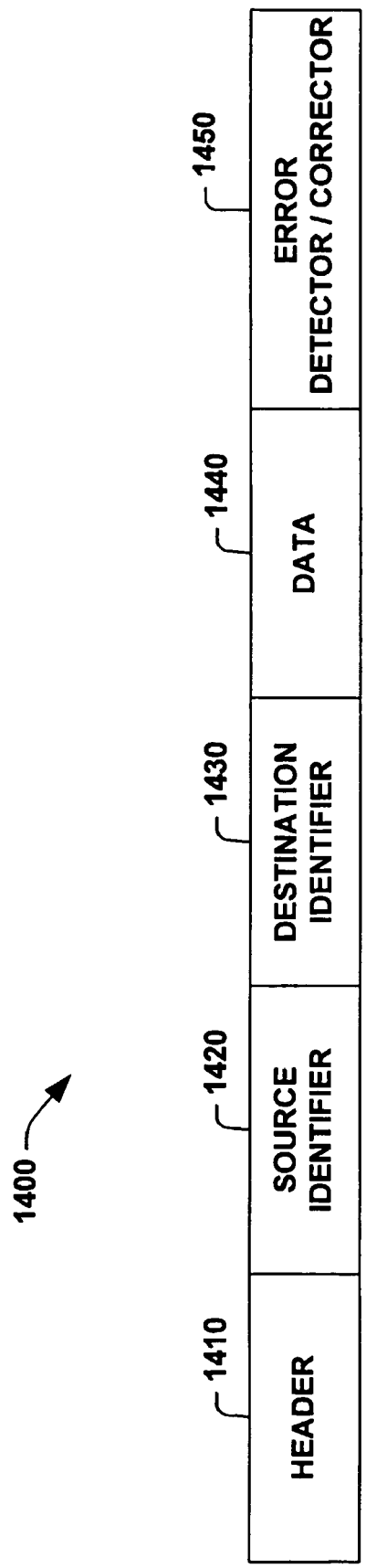
FIG. 14 illustrates an example data packet employed in accordance with an aspect of the present invention.

Referring now to FIG. 14, information can be transmitted between various computer components associated with the systems and methods described herein via a data packet 1400. An exemplary data packet 1400 is shown. The data packet 1400 includes a header field 1410 that includes information like the length and type of packet. A source identifier 1420 follows the header field 1410 and includes, for example, an address of the computer component from which the packet 1400 originated. Following the source identifier 1420, the packet 1400 includes a destination identifier 1430 that holds, for example, an address of the computer component to which the packet 1400 is ultimately destined. Source and destination identifiers can be, for example, globally unique identifiers, URLS (uniform resource locators), path names, and the like. The data field 1440 in the packet 1400 includes various information intended for the receiving computer component. For example, the data field 1440 can hold data including, but not limited to, acquired projection data, object data, fiducial data, corrected projection data, a request for an additional projection data, combinations of these, and so on. The data packet 1400 ends with an error detecting and/or correcting field 1450 whereby a computer component can determine if it has properly received the packet 1400. While six fields are illustrated in the data packet 1400, it is to be appreciated that a greater and/or lesser number of fields can be present in data packets.

Figure 15:
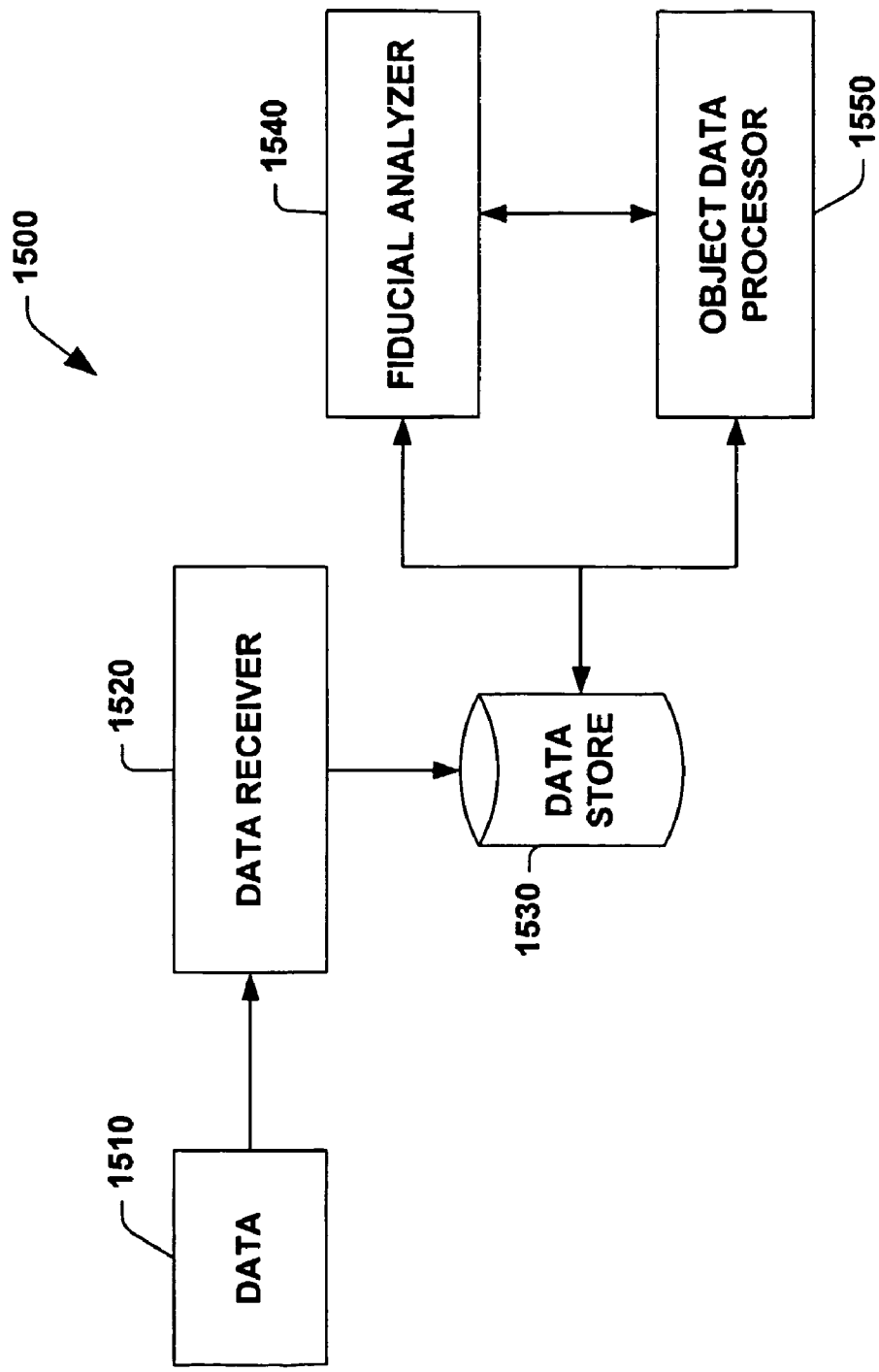
FIG. 15 is a schematic block diagram of an example system for improving the quality of an MRI image degraded by rotational motion during image acquisition.

FIG. 15 is a schematic block diagram of an example system 1500 for improving the image quality of an object where the image is degraded by rotational motion of the object during image acquisition. The system 1500 includes a data receiver 1520 that receives an image data 1510 from the object. The data 1510 can include, but is not limited to, data concerning the object and data associated with a fiducial associated with (e.g., marked on, attached to, located near the object) the object. The data receiver 1520 stores the data in one or more data stores 1530. In one example, the image data is stored in one set of data stores while the fiducial data is stored in a second set of data stores. In another example, the object data and the fiducial data are stored together. The data store 1530 can be, for example, a disk, a tape, a memory (e.g., RAM), and so on. The data store 1530 can store the image data in data structures including, but not limited to, arrays, trees, lists, tables, and so on.

The system 1500 includes a fiducial analyzer 1540 that determines a reference sinusoidal fiducial trajectory data from initial point source data. Furthermore, the fiducial analyzer 1540 examines data from the data store 1530 and computes an actual fiducial trajectory data. The fiducial analyzer 1540 then compares the reference sinusoidal fiducial trajectory data with the actual fiducial trajectory data and stores the result of the comparison.

The system 1500 also includes an object data processor 1550 that selectively manipulates one or more pieces of object data stored in the data store 1530 to facilitate improving the quality of an image that was degraded by rotational motion during image acquisition. The object data processor 1550 undertakes this selective processing based, at least in part, on the comparison produced by the fiducial analyzer 1540.

In one example system 1500, the data 1510 includes one or more projection data of radial k-space data acquired from an MRI device. In another example, the data 1510 is a sinogram data. In one example system 1500, the data 1510 includes a fiducial data that is received from a high signal fiducial mark. The high signal fiducial mark can be, for example, a gadolinium filled tuned fiducial. Another example system 1500 includes a low signal fiducial marker. Another example system 1500 includes a fiducial data filter that removes the fiducial data from the image data to facilitate removing artifacts from a reconstructed image where the artifacts are associated with the fiducial.

The object data processor 1550 can, for example, manipulate object data to improve the quality of an image degraded during image acquisition by rotational motion by performing actions, including but not limited to, deleting projection data, relocating projection data in the data store 1530, and/or combining projection data. In general, the object data processor 1550 modifies the acquired image data so that the fiducial trajectory data more closely resembles or matches the reference trajectory data. Since the system 1500 can produce corrected object data, an extension of the system 1500 can include, for example, an image processor (not illustrated) that produces a viewable image of the object from the manipulated object data. Furthermore, an extension to system 1500 can include a signaler (not illustrated) that generates a control signal indicating that the system 1500 desires one or more additional projection data from the radial k-space. When this additional data is acquired, a data integrator (not illustrated) can integrate the additionally acquired data with previously acquired corrected data. The integration can include, but is not limited to, replacing previously acquired data, averaging with previously corrected data, corrected previously acquired data, and so on. It is to be appreciated that the data receiver 1520, the fiducial analyzer 1540, the object data processor 1550, the image processor, the signaler, and the data integrator, can be computer components as that term is described herein.

Figure 16:
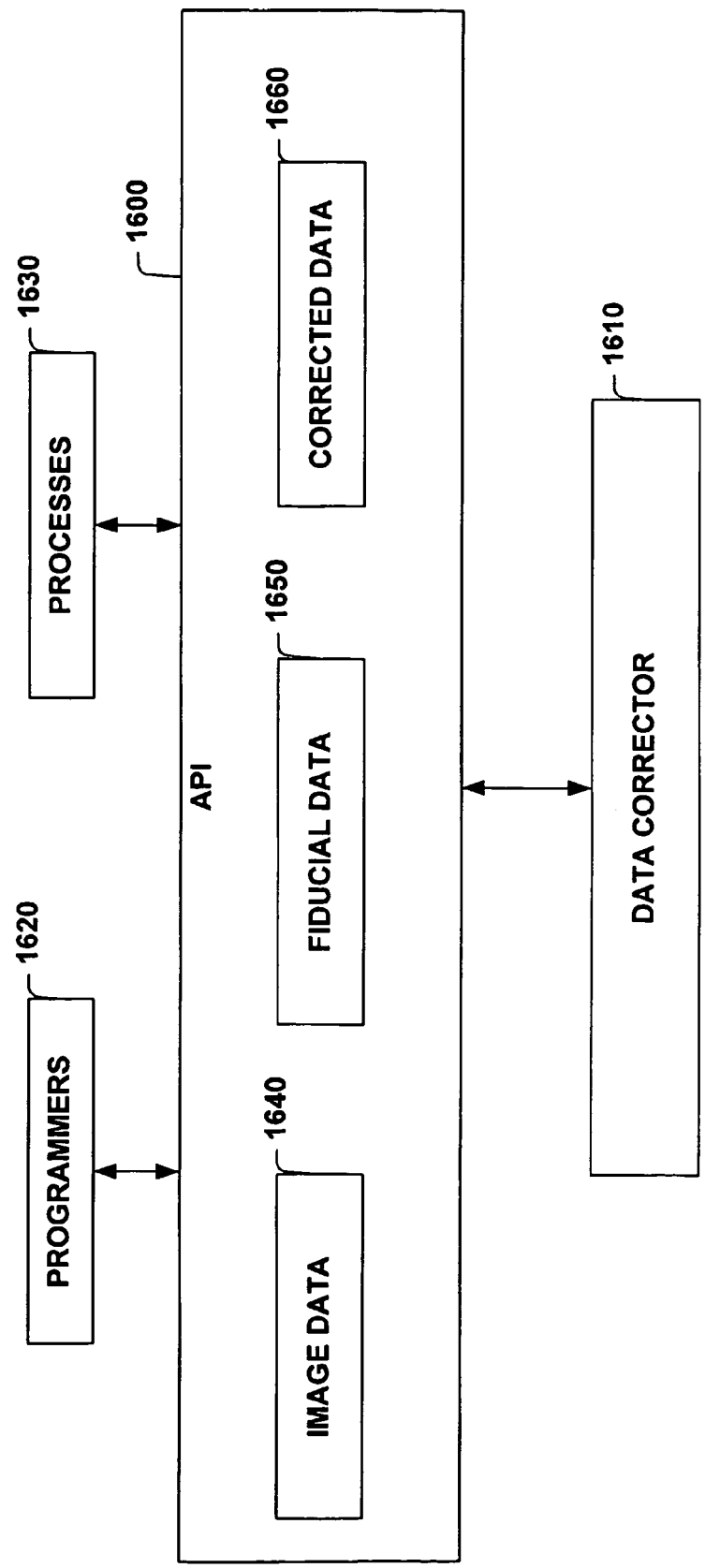
FIG. 16 illustrates an example API employed in accordance with an aspect of the present invention.

Referring now to FIG. 16, an application programming interface (API) 1600 is illustrated providing access to a system 1610 that includes a data corrector. The API 1600 can be employed, for example, by programmers 1620 and/or processes 1630 to gain access to processing performed by the system 1610. For example, a programmer 1620 can write a program to access (e.g., to invoke its operation, to monitor its operation, to access its functionality) a data correcting computer component 1610 where writing such a program is facilitated by the presence of the API 1600. Rather than the programmer 1620 having to understand the internals of the data corrector 1610, the programmer's task is simplified by merely having to learn the interface 1600 to the data corrector 1610. This facilitates encapsulating the functionality of the data corrector 1610 while exposing that functionality. Similarly, the API 1600 can be employed to provide data values to the system 1610 and/or to retrieve data values from the system 1610. For example, a programmer 1620 may wish to present image data to the data corrector 1610 and thus the programmer 1620 may employ an image data interface 1640 component of the API 1600. Similarly, the programmer 1620 may wish to present fiducial data to the data corrector 1610 and thus may employ a fiducial data interface 1640 component of the API 1600. After receiving the image data and fiducial data, the data corrector 1610 may, for example, pass corrected data to a process 1630 via a corrected data interface 1660 component of the API 1600.

Thus, in one example of the API 1600, a set of application program interfaces can be stored on a computer-readable medium. The interfaces can be executed by a computer component to gain access to a data corrector. Interfaces can include, but are not limited to, a first interface that receives and/or returns an image data associated with an image, a second interface that receives and/or returns a fiducial data associated with a fiducial, and a third interface that receives and/or returns a corrected image data generated from the image data and the fiducial data.

The systems, methods, and objects described herein may be stored, for example, on a computer readable media. Media can include, but are not limited to, an application specific integrated circuit (ASIC), a compact disc (CD), a digital versatile disk (DVD), a random access memory (RAM), a read only memory (ROM), a programmable read only memory (PROM), a disk, a carrier wave, a memory stick, and the like.

Thus, an example computer readable medium can store computer executable instructions for a computer implemented method for reducing the effects on image quality of rotational motion of an object during image acquisition. The method includes receiving a point source data associated with a fiducial associated with the object to be imaged and computing a point source location based on the point source data. The method then computes a predicted sine wave data based on the point source location and/or the point source data. The method includes receiving an observed image data that has a set of projection data associated with the object to be imaged, and an observed waveform data associated with the predicted sine wave data. Once the observed image data is retrieved, the method compares the predicted sine wave data with the observed waveform data and selectively processes the observed image data to reduce the effects of rotational motion of the imaged object. The processing can include, but is not limited to, removing projection data, reordering projection data, and acquiring additional projection data.

Similarly, a computer readable medium can store computer executable components of a system for improving the image quality of an object degraded by rotational motion of the object during image acquisition. The system includes a data receiving component for receiving an image data from the object, where the image data includes object data and fiducial data. The system also includes data stores for storing the object data and the fiducial data, either individually or collectively. A fiducial analyzer determines a reference sinusoidal fiducial trajectory data and an actual fiducial trajectory data and then compares the two trajectory data. An object data processor selectively manipulates the object data to improve the quality of an object image degraded by rotational motion of the object based.

Figure 17:
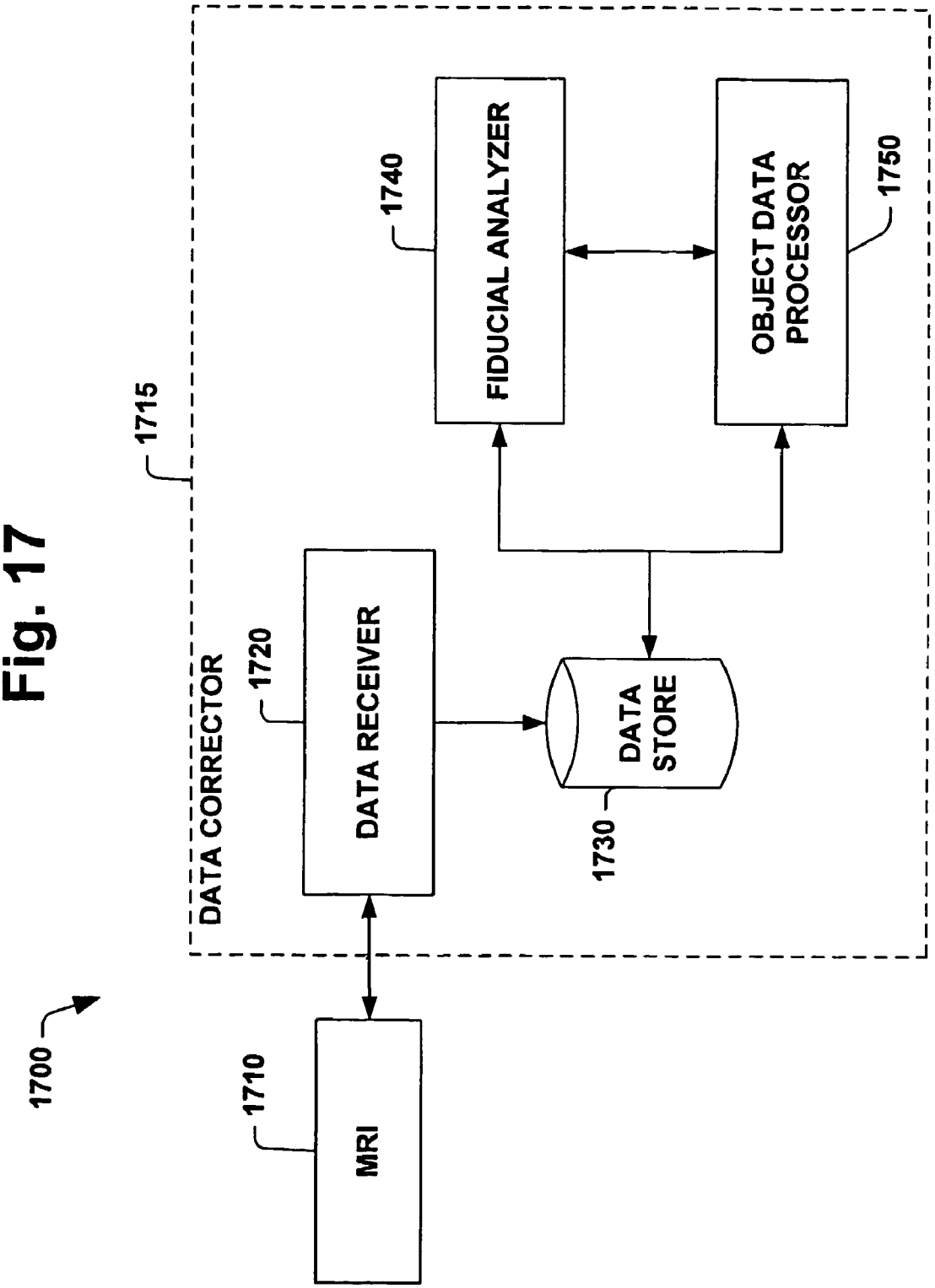
FIG. 17 illustrates an example MRI system interacting with a data corrector.

FIG. 17 illustrates an example system 1700 in which an MRI system 1710 interacts with a data corrector 1715. The data corrector 1715 can include, for example, a data receiver 1720, a data store 1730, a fiducial analyzer 1740, and an object data processor 1750, substantially similar to the computer components described in FIG. 15. The MRI system 1710 can be operably connected to the data receiver 1720 by techniques including, but not limited, direct connections, local area network, wide area network, satellite communications, cellular communications, and so on.

FIG. 18 illustrates an example MRI system 1800 that includes computer components that form a data corrector. The components of the data corrector include, but are not limited to, a data receiver 1820, a data store 1830, a fiducial analyzer 1840, and an object data processor 1850 that are substantially similar to the computer components described above in connection with FIG. 15.

What has been described above includes several examples. It is, of course, not possible to describe every conceivable combination of components or methodologies for purposes of describing the methods, systems, computer readable media and so on employed in improving the quality of MRI images affected by rotational motion of the object being imaged. However, one of ordinary skill in the art may recognize that further combinations and permutations are possible. Accordingly, this application is intended to embrace alterations, modifications, and variations that fall within the scope of the appended claims. Furthermore, to the extent that the term "includes" is employed in the detailed description or the claims, it is intended to be inclusive in a manner similar to the term "comprising" as that term is interpreted when employed as a transitional word in a claim.

What is claimed is:

1. A computer implemented method for reducing the effects on image quality of rotational motion of an object during image acquisition, the method comprising:

receiving a point source data associated with a fiducial associated with the object, the point source data being acquired from at least a first projection data ($S_1$) acquired at a first time $T_1$ from a first viewing angle $\theta_1$ resulting in a first projected distance $r_1$ and a second projection data ($S_2$) acquired at a second time $T_2$ from a second viewing angle $\theta_2$ resulting in a second projected distance $r_2$;

computing a point source location based, at least in part, on the point source data;

computing a predicted sine wave data based, at least in part, on at least one of the point source location and the point source data;

receiving an observed image data comprising:
one or more projection data of a radial k-space associated with the object; and
an observed waveform data related to a location of the fiducial associated with the object and further associated with the predicted sine wave data;

comparing the predicted sine wave data and the observed waveform data; and selectively processing the observed image data to reduce the effects of rotational motion of the object based, at least in part, on the comparison of the predicted sine wave data and the observed waveform data;

where computing the point source location comprises:
determining $R_{res}$, where $R_{res}$ is the displacement component of a polar coordinate for the point source; and
determining $\theta_{res}$, where $\theta_{res}$ is the angular component of the polar coordinate for the point source.

2. The method of claim 1, where $R_{res}$ is determined according to $R_{res}$=square root $(r_1^2+r_2^2)$, where $r_1$ is a first projected distance of a Cartesian coordinate for the first projection data of the point source and where $r_2$ is a second projected distance of a Cartesian coordinate for the second projection data of the point source.

3. The method of claim 2, where $\theta_{res}$ is determined according to $\theta_{res}=\tan^{-1} (r_2/r_1)$.

4. The method of claim 3, where computing the predicted sine wave comprises calculating the predicted sine wave from $R_{res}$ and $\theta_{res}$.

5. The method of claim 4, where the predicted sine wave is calculating according to $\sin_{res}=(R_{res}) \cos (|\theta_{res}-\theta|)$, where $\theta$ varies between a plurality of viewing angles.

* * * * *

UNITED STATES PATENT AND TRADEMARK OFFICE
CERTIFICATE OF CORRECTION

| | | |
|---|---|---|
| PATENT NO. | : 7,002,342 B2 | |
| APPLICATION NO. | : 10/475382 | |
| DATED | : February 21, 2006 | |
| INVENTOR(S) | : Duerk et al. | |

It is certified that error appears in the above-identified patent and that said Letters Patent is hereby corrected as shown below:

On The Title Page Item (57)
Please replace abstract with this substitute abstract to remove inserted reference numbers and to correct a typographical error:

A method and system for improving image quality by correcting errors introduced by rotational motion of an object being imaged is provided. The method provides a computer executable methodology for detecting a rotation and selectively reordering, deleting and/or reacquiring projection data.

Col. 1, Line 3 the following is inserted:

Portions of the claimed subject matter where developed with federal funding supplied under NIH grants R01 CA81431-02 and R33 CA88144-01. The U.S. government may have certain rights in the invention.

Signed and Sealed this

Twenty-second Day of August, 2006

JON W. DUDAS
*Director of the United States Patent and Trademark Office*